United States Patent [19]

Imondi

[11] Patent Number: 5,114,947
[45] Date of Patent: May 19, 1992

[54] METHOD FOR ALLEVIATING ANXIETY USING BENZOBICYCLIC CARBOXAMIDES

[75] Inventor: Anthony R. Imondi, Westerville, Ohio

[73] Assignee: Erbamont Inc., Dublin, Ohio

[21] Appl. No.: 634,648

[22] Filed: Dec. 27, 1990

[51] Int. Cl.⁵ .................. A61K 31/41; A61K 31/44
[52] U.S. Cl. ...................................... 514/282; 514/359
[58] Field of Search ........................ 514/282, 359

Primary Examiner—S. J. Friedman
Attorney, Agent, or Firm—Thompson, Hine and Flory

[57] ABSTRACT

Benzofuran—7—carboxamides with anxiolytic activity.

27 Claims, No Drawings 5,114,947

1

METHOD FOR ALLEVIATING ANXIETY USING BENZOBICYCLIC CARBOXAMIDES

BACKGROUND

The present invention is based upon the discovery that benzofuran-7-carboxamides, and related compounds, and, more particularly, pyrrolidinyl and quinuclidinyl derivatives thereof exhibit strong anxiolytic activity.

Commonly assigned U.S. Pat. No. 4,888,353 to Lednicer discloses a novel group of compounds including benzofurancarboxamides and dihydrobenzofurancarboxamides and their quinuclidinyl derivatives which are useful as antiemetic and antipsychotic agents.

It has previously been disclosed in U.S. Pat. No. 4,857,517 to Youssefyeh that certain quinuclidinyl benzoxepins such as 6-amino-7-chloro-9-N-(1-azabicyclo[2.2.2]octan -3-yl)carboxamido-2,3,4,5-tetrahydro-1-benzoxepin are 5HT$_3$ antagonists and are considered to be useful in the treatment of schizophrenia, anxiety and migraine. European Application 0 307 172 discloses that certain benzofurancarboxamides such as endo-5-chloro-2,3-dihydro-2,2-dimethyl-N-(8-methyl-8-azabicyclo [3.2.1] oct-3-yl)-7-benzofurancarboxamide (Z)-2-butenedioate and 2,3-dihydro-5-chloro-2,2-dimethyl-N-(1-azabicyclo[2.2.2] oct -3-yl-7-benzofuran carboxamide (Z)-2-butenedioate are 5HT$_3$ antagonists.

According to Gardner, "Potential use of Drugs Modulating 5HT Activity in the Treatment Anxiety," *Gen Pharmacol*, 1988 19(3) p 347–56, while it has been suggested that 5HT mediated systems may be involved in modulating anxiety, the premise has been questioned and the mechanism remains unknown. 5-Hydroxytryptophan (5HT), also known as Serotonin, is found throughout the body and is involved in a large number of physiological processes related to a variety of different receptors found on the surface membranes of cells in different body tissues There appear to be a large number of 5HT receptor types, some experts estimating there may be in excess of 20, and some drugs are believed to have different effects on different receptors all of which contribute to the overall effect of the drug. Consequently, the physiological activity of 5HT antagonists remains highly unpredictable.

Accordingly, while it has been claimed that certain carboxamides are 5HT$_3$ antagonists and possess anxiolytic activity, this does not indicate that there is even a strong likelihood that other 5HT$_3$ antagonists will relieve anxiety. For example, File and Johnston, *Psychopharmacology*, (1989) 99: 248–251 report that three 5HT$_3$ antagonists including A. H. Robin's Zacopride had no significant effect on social interaction in the elevated plug-maze test in the rat.

SUMMARY OF THE INVENTION

The present invention is directed to a method for treating anxiety in a patient comprising administering to said patient an anxiolytically effective amount of a compound of formula I described below.

The present invention is more particularly directed to a method for treating anxiety using benzofurancarboxamides or dihydrobenzofurancarboxamides of the formula (VIII) or (IX) below.

The invention is still more particularly directed to a method in which the moiety designated by A in formula (I), (VIII) or (IX) is a quinuclidinyl group or a pyrrolidinyl group.

A more particular object of the invention is to provide a method for treating anxiety using the compound, N-(1-azabicyclo [2.2.2]oct-3-yl)-4-amino-5-chloro-2,3-dihydrobenzo[b]furan -7-carboxamide (Compound 77) or the compound 4-amino-5-chloro-N -pyrrolidinylmethyl-2,3-dihydrobenzo[b]furan-7-carboxamide (Compound 75) or pharmaceutically acceptable salts thereof.

A still more particular object of the invention is the use of the R-isomers of the foregoing compounds.

DETAILED DESCRIPTION OF THE INVENTION

The present invention is directed to a method of treating anxiety comprising administering to a patient in need of such treatment an anxiolytically effective amount of a compound of formula (I):

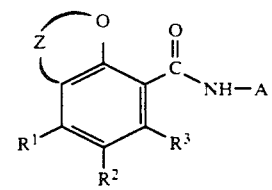

wherein Z represents the carbon and hydrogen atoms necessary to complete a substituted or unsubstituted, saturated or unsaturated, 5- to 7-membered ring; $R^1$, $R^2$, and $R^3$ may be the same or different and represent hydrogen, lower alkyl, cycloalkyl, lower alkoxy, amino, lower alkyl substituted amino, acylamido, sulfonamido, halogen or nitro group; provided that when Z represents the atoms necessary to complete a 2,3,4,5-tetrahydro-1-benzoxepin ring, $R^1$ may not equal hydrogen, amino or alkylamino and $R^2$ may not equal hydrogen or halogen; further provided that when Z represents the atoms necessary to complete a 2,2-dimethyl-2,3-dihydrobenzofuran ring, $R^1$, $R^2$ and $R^3$ may not simultaneously equal hydrogen, and when $R^2$ is flourine $R^1$ and $R^3$ may not equal hydrogen; still further provided that when Z represents the atoms necessary to complete a 2,2-dimethyl or a 2,2-diethyl 3,4-dihydrobenzopyran ring, $R^2$ may not equal fluorine or chlorine when $R^1$ and $R^3$ are hydrogen; A represents a group of the formula (II), (III), (IV), (V), (VI), or (VII).

(II)

(III)

(IV)

-continued

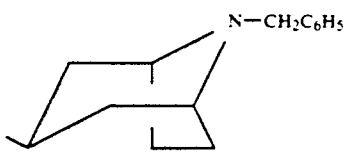 (V)

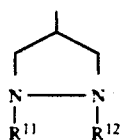 (VI)

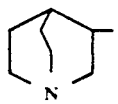 (VII)

in which W represents a single bond or the carbon and hydrogen atoms necessary to complete a 3- to 8-membered saturated or an unsaturated ring; Y represents a single bond or the carbon and hydrogen atoms necessary to complete a 4- to 8-membered saturated or unsaturated ring; $R^6$ is hydrogen, lower alkyl, phenyl, phenalkyl, fluorine-substituted alkyl, propargyl, or allyl; $R^7$ and $R^8$ may be the same or different and are equal to hydrogen, lower alkyl, or lower hydroxyalkyl; $M^1$ and $M^2$ are the same or different and represent hydrogen, or methyl; $R^{11}$ and $R^{12}$ are the same or different and represent lower alkyl, cycloalkyl, or phenalkyl; n is 0 or an integer of 1 to 3.

In some preferred embodiments of the invention, A represents a group of the formulas (IIa), (IIIa), or (IVa):

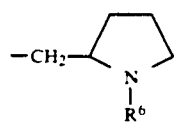 (IIa)

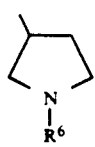 (IIIa)

—CH$_2$CH$_2$NR$^7$R$^8$ (IVa)

wherein $R^6$, $R^7$ and $R^8$ are defined as in formula I above.

The present invention is more specifically directed to the anxiolytic use of benzo[b]furan and dihydrobenzo[b]furancarboxamides represented by the formulas (VIII) and (IX) wherein $R^1$, $R^2$, and $R^3$ are defined as above and $R^9$, $R^{9A}$, and $R^{9B}$ are selected from the group consisting of hydrogen, C1-3 alkyl or phenyl; and to pharmaceutical preparations containing these compounds as the active drug substance.

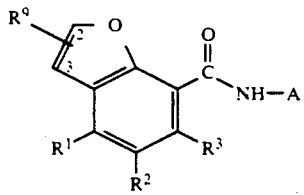 (VIII)

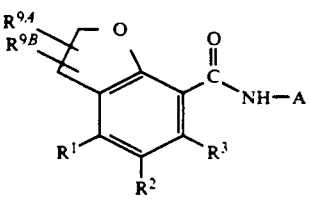 (IX)

The present invention is still more specifically directed to the use of compounds of the formulas (I), (VIII), or (IX) wherein A is represented by the formula (IIa) or the formula (VII) and pharmaceutical compositions containing the same. Compounds are particularly preferred in which A is represented by the formula (IIa) or (VII) and $R^1$ is amino, $R^2$ is chlorme, and $R^3$ is hydrogen. Still more preferably in formula (IIa), $R^6$ is hydrogen.

As described herein, the moiety, Z represents the atoms necessary to complete a 5- to 7-membered saturated or unsaturated oxygen containing ring for example, benzo[b]furan, dihydrobenzo[b]furan, benzoxepin, etc. In the preferred compounds Z forms a benzo[b]furan or a dihydrobenzo[b]furan ring which may be unsubstituted or monosubstituted or disubstituted in the 2- or 3-position by lower alkyl for example, methyl or ethyl; or phenyl. Where Z represents the atoms necessary to form a dihydrobenzo[b]furan ring, Z may be represented by the formula $C_nH_{2n}$ where n is 2 to 4 such as —CH$_2$CH$_2$—, —CH$_2$CH(CH$_3$)—, —C(CH$_3$)$_2$CH$_2$—, —CH$_2$C(CH$_3$)$_2$—, —CH(CH$_3$)CH$_2$—, —CH$_2$CH(C$_2$H$_5$)—, etc. Where Z represents the atoms necessary to form a benzofuran ring, Z may represent —CH=CH—, —CH=CCH$_3$—, or —CH$_3$C=CH—. Alternatively, Z may include a phenyl group at the 2- or 3-position.

The term "lower alkyl group" as used herein includes straight or branched chain alkyl groups of about 1 to 6 carbon atoms such as methyl, ethyl, propyl, i-propyl, n-butyl, t-butyl, amyl, isoamyl, n-hexyl, etc.

The term "lower alkoxy group" as used herein includes alkoxy groups which correspond to the aforementioned alkyl groups with the addition of the —O— linkage.

The term "phenyl group" and "phenalkyl group" as used herein include groups in which the phenyl moiety is unsubstituted or substituted by substituents such as methyl, ethyl, propyl, butyl, fluoro, chloro, bromo, iodo, amino, hydroxyl, methoxy, ethoxy, cyano, acetamido, sulfamoyl, and trifluoromethyl. Examples of phenalkyl groups include benzyl, phenethyl and phenylpropyl groups.

The term "cycloalkyl group" as used herein includes cycloalkyl groups containing up to 12 carbon atoms and preferably 4 to 8 carbon atoms such as cyclobutyl, cyclohexyl, cyclopentyl, ethylcyclohexyl.

Representative examples of the substituent groups represented by $R_1$, $R_2$, or $R_3$ include methyl, ethyl, n-propyl, i-propyl, and t-butyl groups.

Subject to the exclusions noted above, representative examples of the halogen atoms represented by $R^1$, $R^2$, and $R^3$ include fluorine, chlorine, bromine and iodine atoms.

The amino group represented by $R^1$, $R^2$, or $R^3$ may be an unsubstituted amino group or a substituted amino group of the formula —$NR^4R^5$ wherein $R^4$ and $R^5$ may be the same or different and selected from a hydrogen atom or a lower alkyl group. Otherwise, the amino group can be a substituted amino group such as an acylamido (e.g., acetamido) or a sulfonamido group of the formulae —$NHCOR^4$ and —$NHSO_2R^4$ wherein $R^4$ is defined as above.

Representative examples of the alkoxy groups for $R^1$, $R^2$, and $R^3$ include methoxy, ethoxy, and propoxy.

In the formula (II), W most preferably represents the atoms necessary to complete a pyrrolidinyl ring A particularly advantageous compound is obtained when $R^6$ in formula (IIa) represents a hydrogen atom such that A is a 2-pyrrolidinylmethyl group. Otherwise, $R^6$ is preferably ethyl, benzyl, allyl, or propargyl.

In formula (III), Y may represent the atoms necessary to complete a 3-pyrrolidinyl ring, and $R^6$ may be benzyl.

In formula (IV), $M^1$ and $M^2$ are preferably hydrogen and $R^7$ and $R^8$ are both ethyl, both hydroxyethyl, or one of $R^7$ and $R^8$ is ethyl and the other hydroxyethyl.

In formula (VI), $R^{11}$ and $R^{12}$ may be the same or different and represent a methyl group, an ethyl group, an isopropyl group, a cyclobutyl group, a cyclopentyl group, a cyclohexyl group, and ethylcyclohexyl group, a benzyl group, or a phenpropyl group.

Compounds of particular usefulness are compounds in which A has the formula (VII) or the formula (IIa) and $R^1$, $R^2$, and $R^3$ are defined as follows:

| | | |
|---|---|---|
| $R^1$ = H | $R^2$ = Cl | $R^3$ = H |
| $R^1$ = H | $R^2$ = $NH_2$ | $R^3$ = H |
| $R^1$ = $NH_2$ | $R^2$ = Cl | $R^3$ = H |
| $R^1$ = H | $R^2$ = H | $R^3$ = $OCH_3$ |

The compounds of the invention may be used as the active drug substance in pharmaceutical compositions in the form of the free base, in the form of a salt, e.g., an acid addition salt, and as a hydrate. All forms are within the scope of this invention. Suitable addition salts are, for example, including the maleate, hydrochloride, phosphate, fumarate, citrate, tartarate. Many of the compounds of the present invention contain an asymmetric carbon atom and have optical isomers. Compounds in which A is IIa or VII, may be more active as the R-isomer. In early studies, the R-isomer of compound 75 and compound 77 appear to be more anxiolytically active than its corresponding S-isomer. Similarly, the amido group in some compounds have an endo or exo orientation one of which may be more active than the other.

Representative examples of compounds in accordance with the present invention are shown in Table I. In some instances Table I designates a particular isomer, however, regardless of whether a particular isomer is designated or not, the invention includes the racemate as well as the isolated isomers.

TABLE

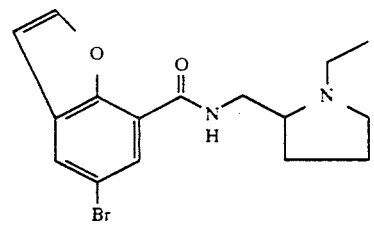

1.

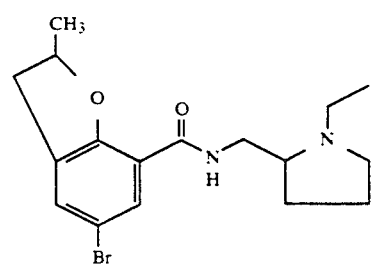

2.

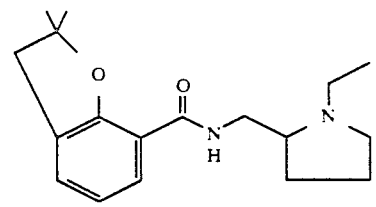

3.

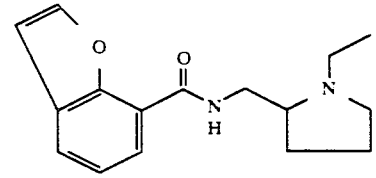

4.

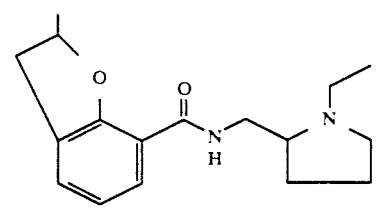

5.

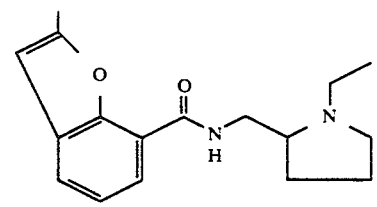

6.

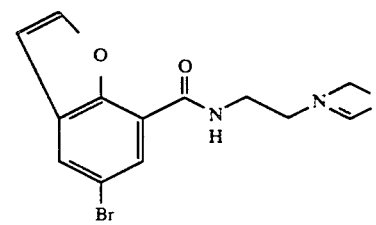

7.

TABLE-continued
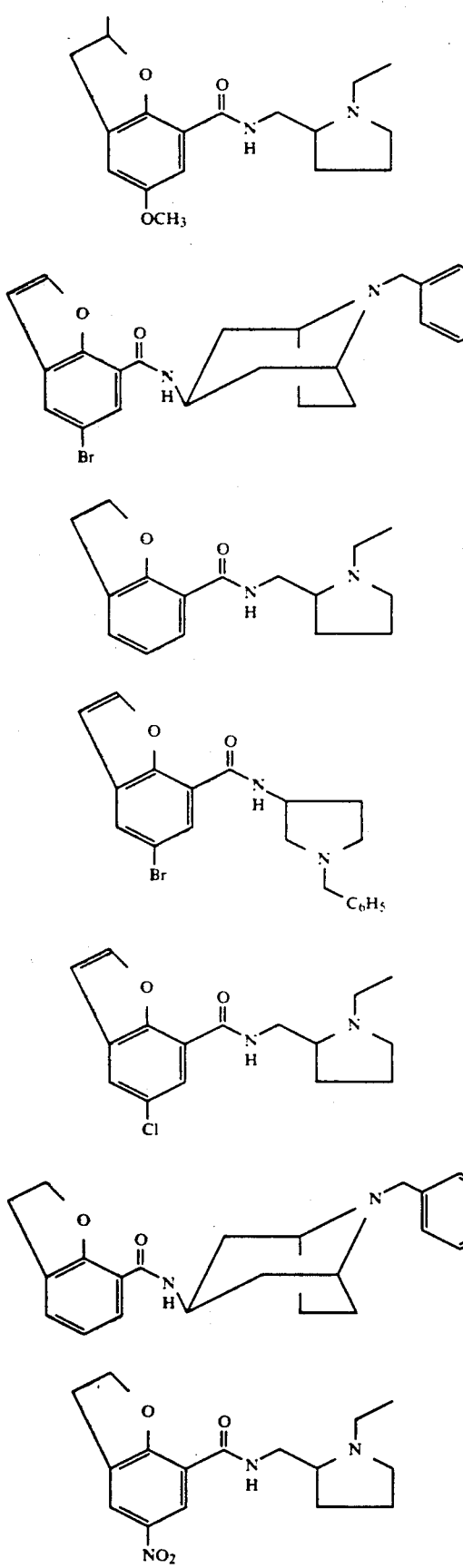
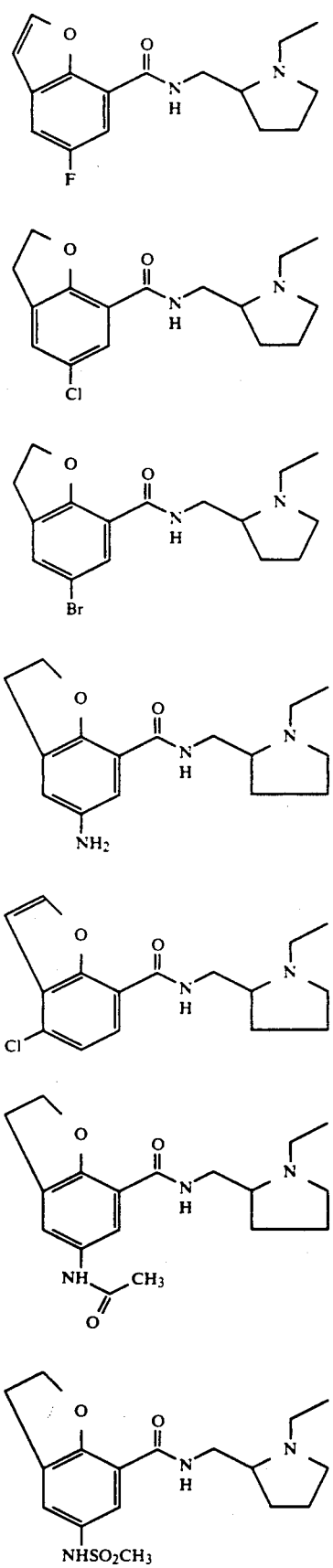

TABLE-continued
22. 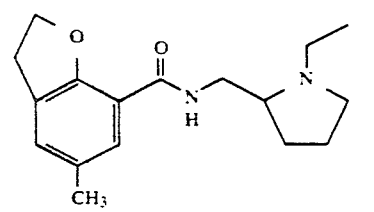
23. 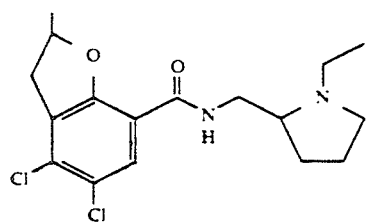
24. 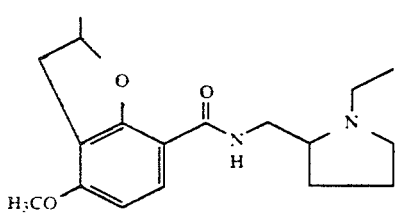
25. 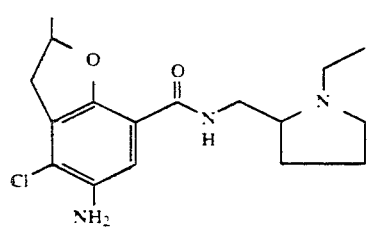
26. 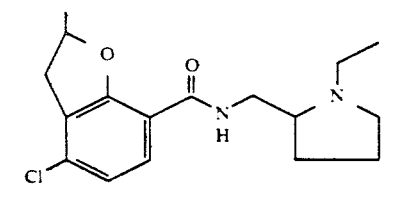
27. 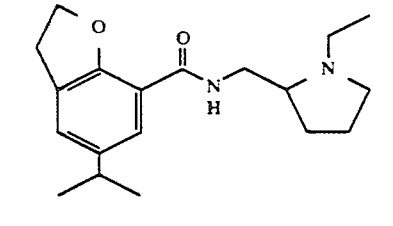
28. 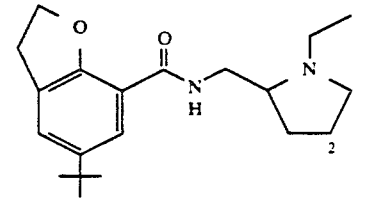
TABLE-continued
29. 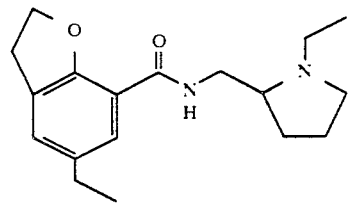
30. 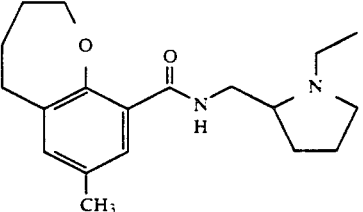
31. 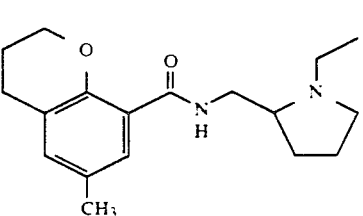
32. 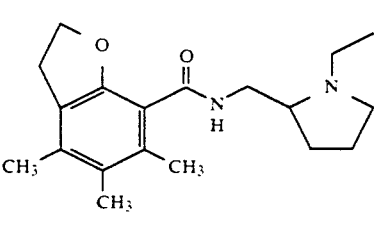
33. 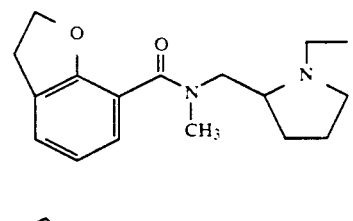
34. 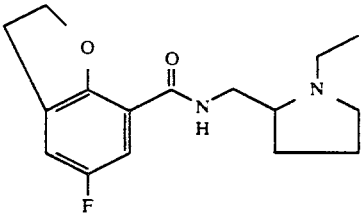
35. 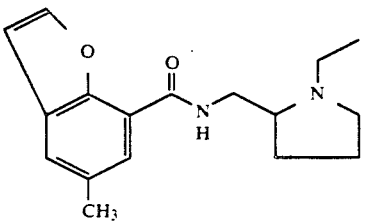

TABLE-continued
| | |
|---|---|
| 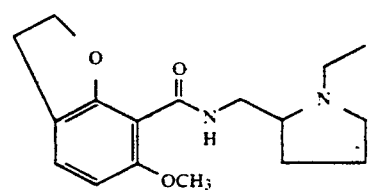 36. | 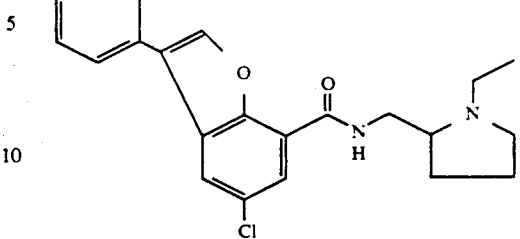 43. |
| 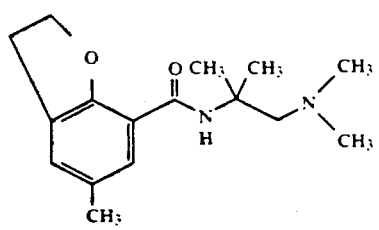 37. | 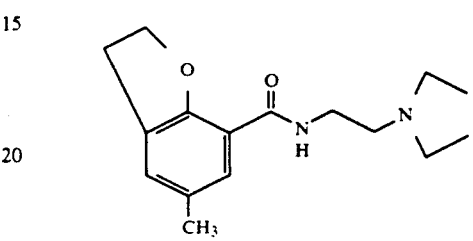 44. |
| 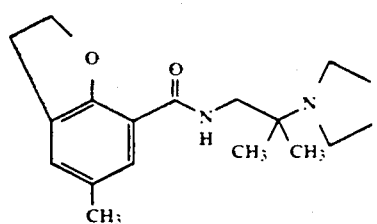 38. | 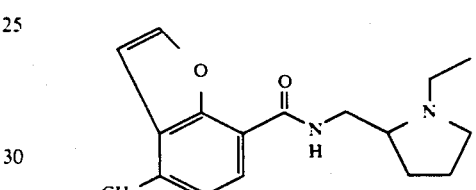 45. |
| 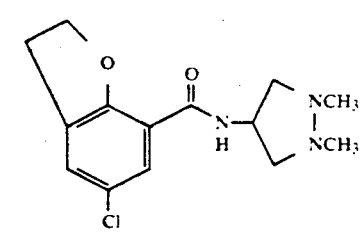 39. | 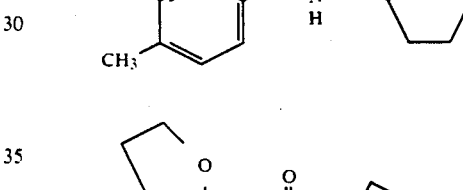 46. |
| 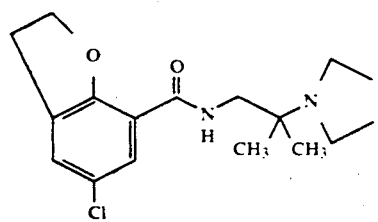 40. | 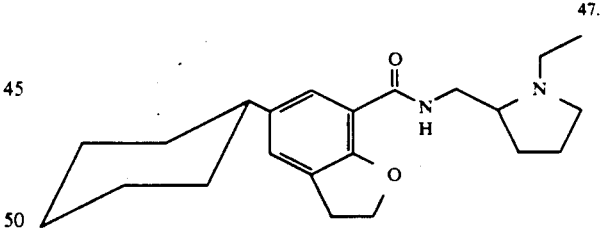 47. |
| 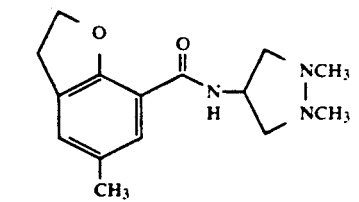 41. | 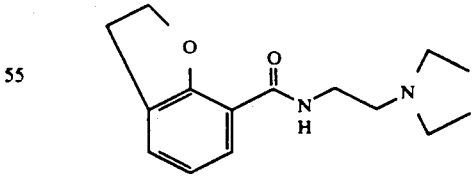 48. |
| 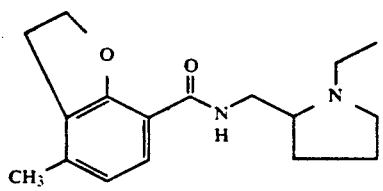 42. | 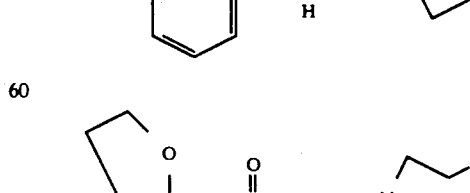 49. |

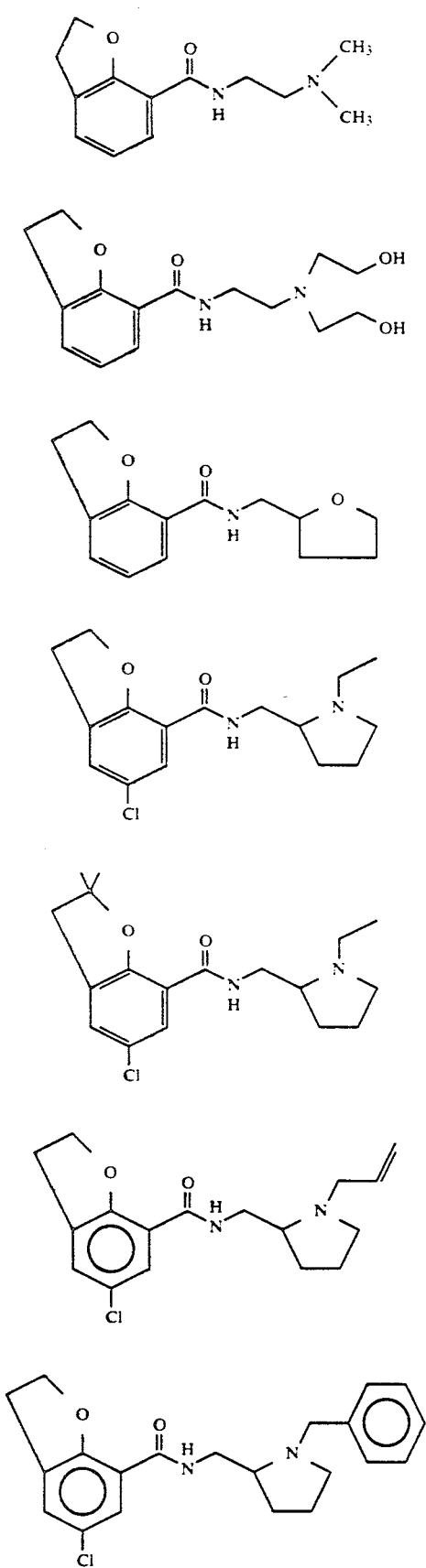
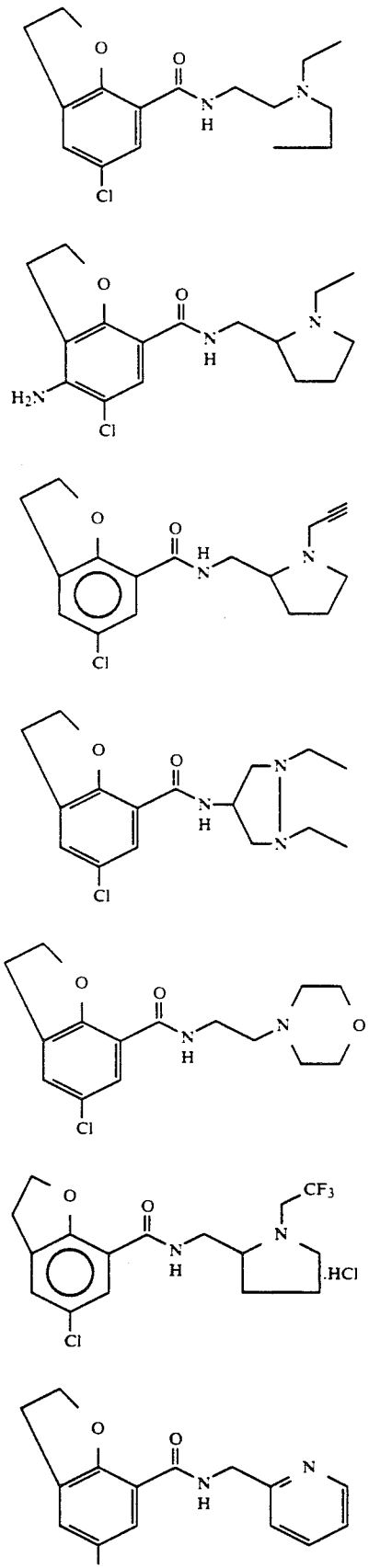

TABLE-continued
64. 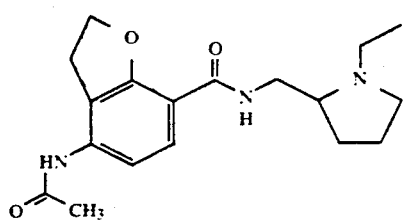
65. 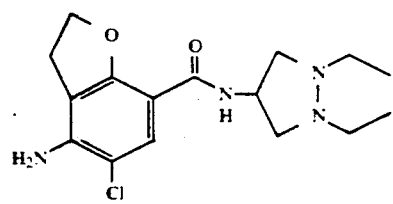
66. 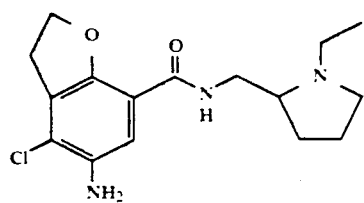
67. 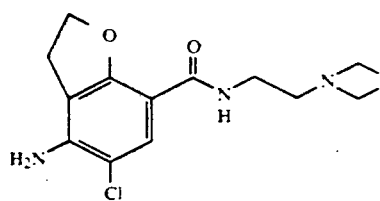
68. 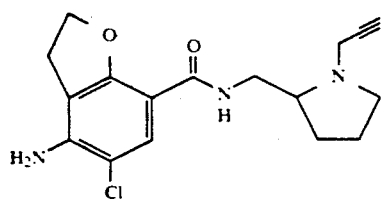
69. 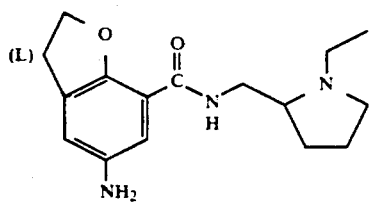
70. 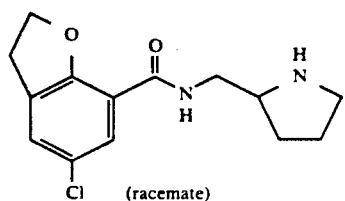
(racemate)
TABLE-continued
71. 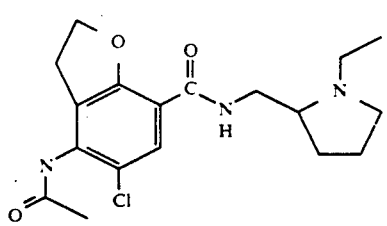
72. 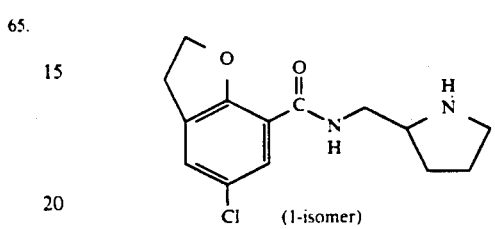
(1-isomer)
73. 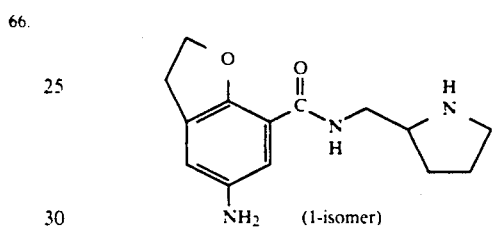
(1-isomer)
74. 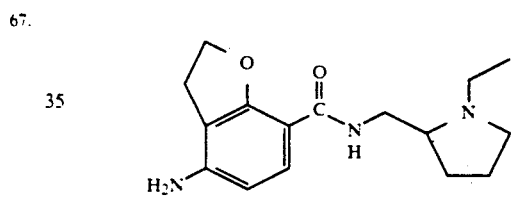
75. 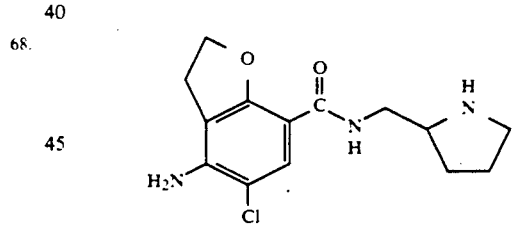
76. 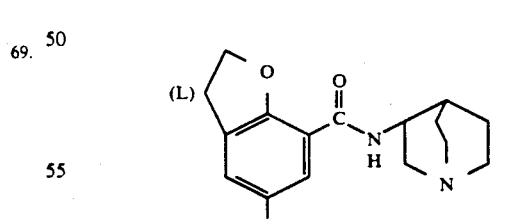
(1-isomer)
77. 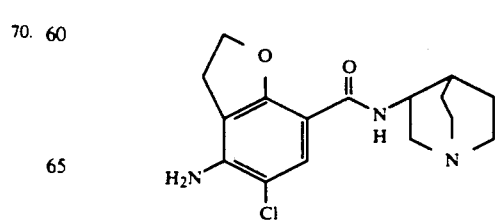

TABLE-continued
| # | |
|---|---|
| 78. | 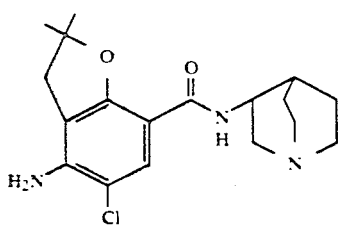 |
| 79. | 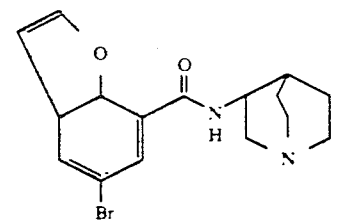 |
| 80. | 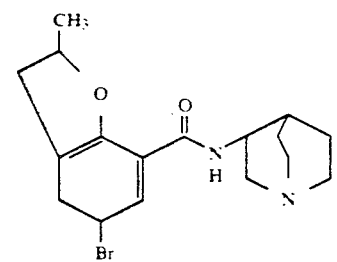 |
| 81. | 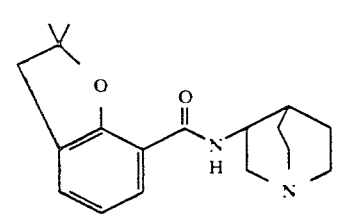 |
| 82. | 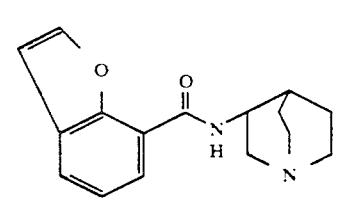 |
| 83. | 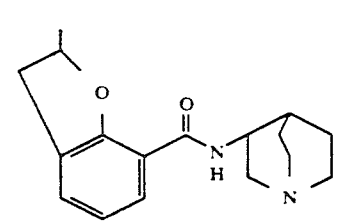 |
| 84. | 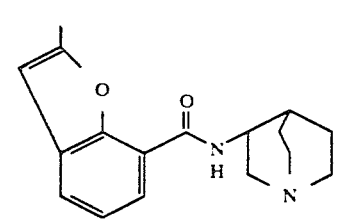 |
TABLE-continued
| # | |
|---|---|
| 85. | 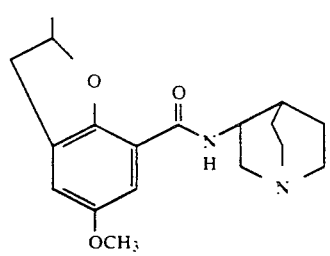 |
| 86. | 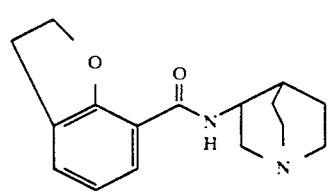 |
| 87. | 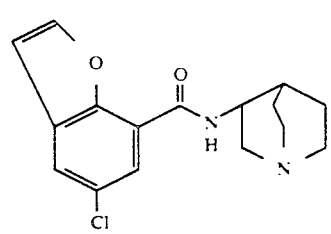 |
| 88. | 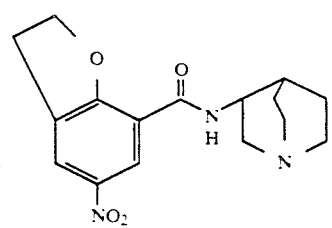 |
| 89. | 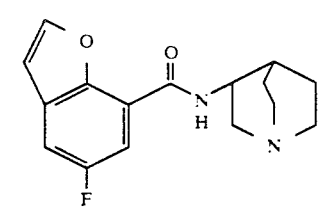 |
| 90. | 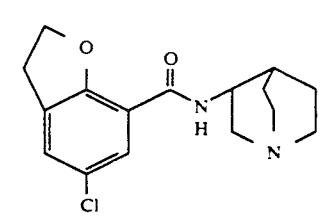 |
| 91. | 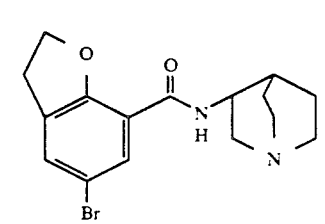 |

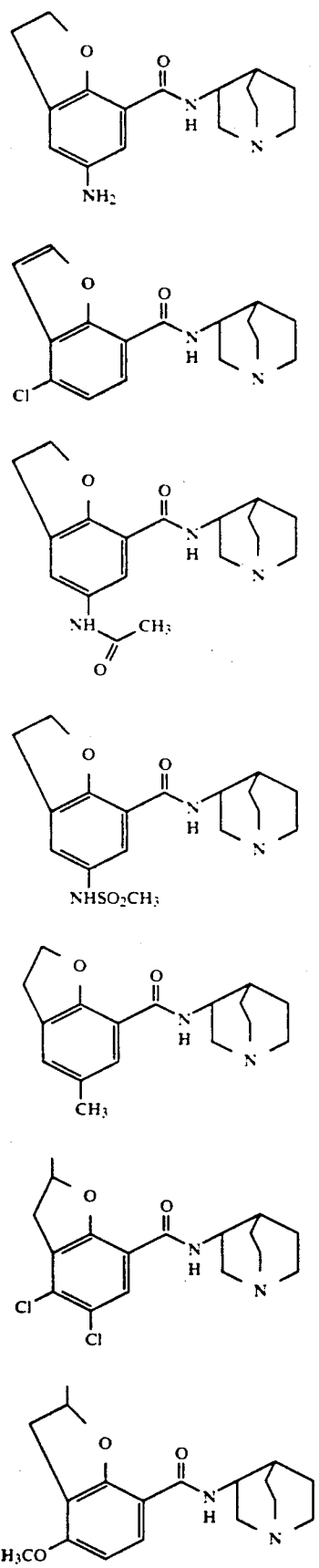
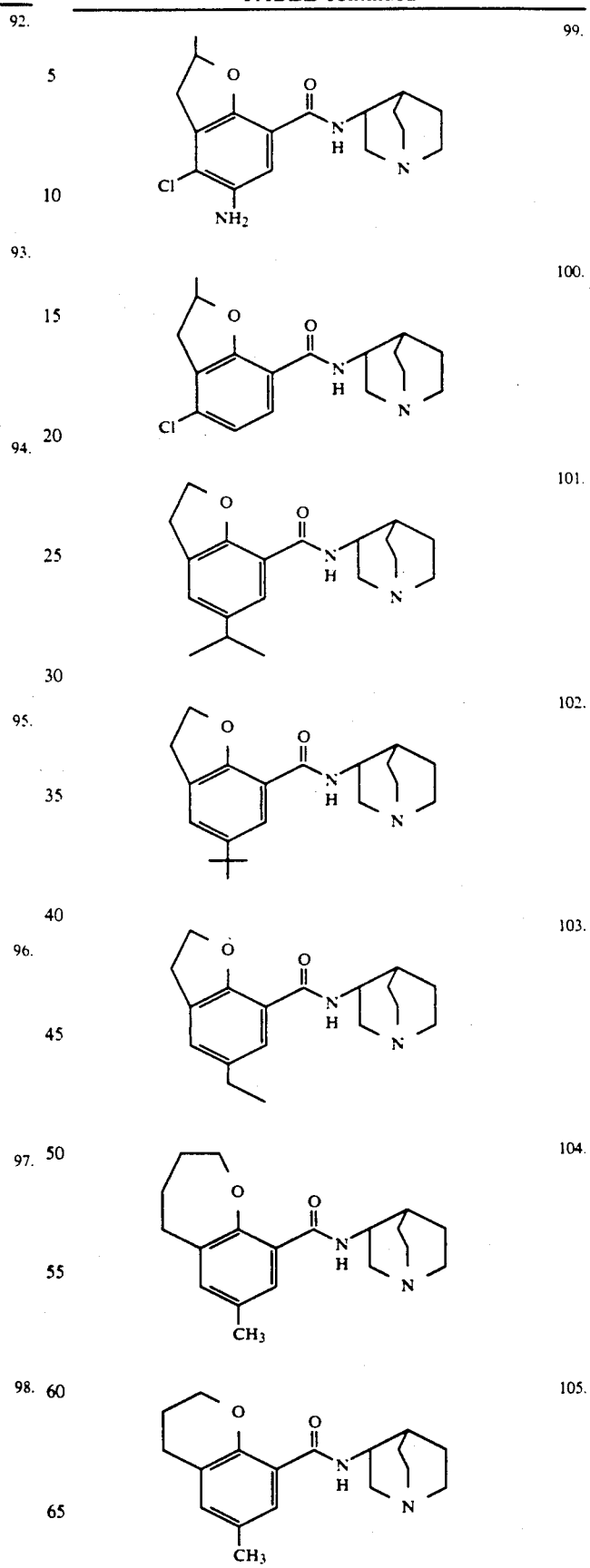

TABLE-continued
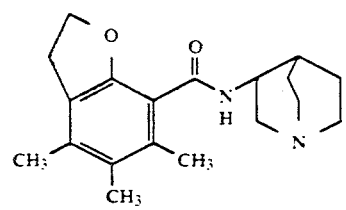 106.
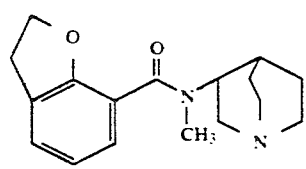 107.
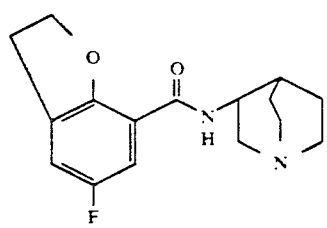 108.
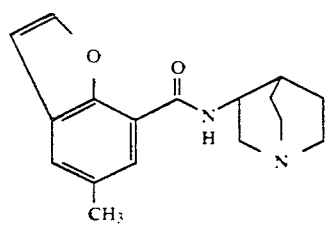 109.
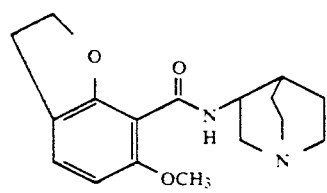 110.
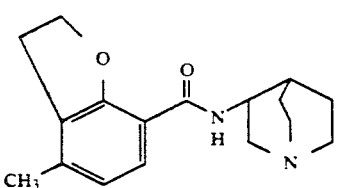 111.
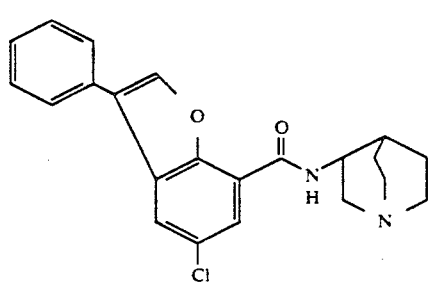 112.
TABLE-continued
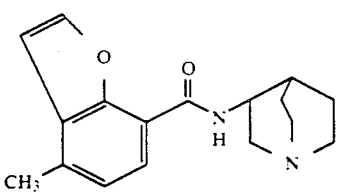 113.
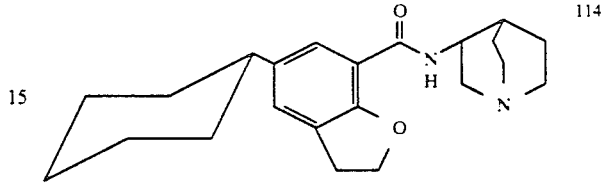 114.
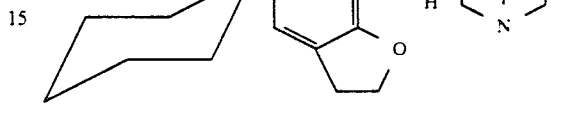 115.
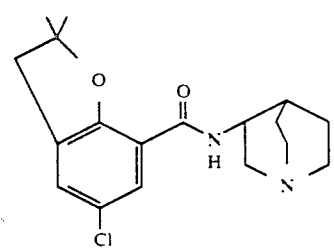 116.
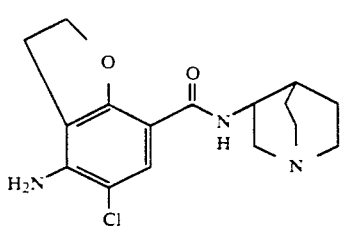 117.
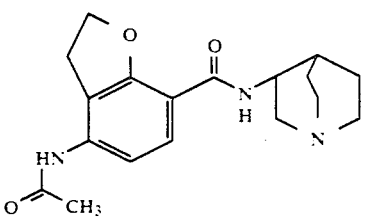 118.
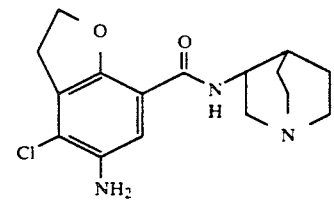 119.

TABLE-continued

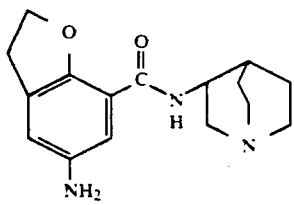

120.

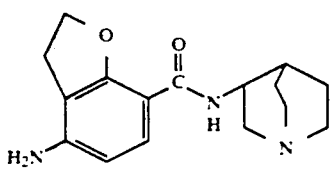

121.

Typically, the optically active isomers are prepared from the optically active amine which is condensed with the acid to produce the carboxamide. Optically active 3-aminoquinuclidine is commercially available from Chiron Laboratory, Trondheim, Norway The chemical syntheses of the anxiolytic agents described herein are described in detail in U.S. Pat. No. 4,888,353 to Lednicer. In many instances, the compounds of the present invention can be prepared by condensing benzo[b]furan -7-carboxylic acid or dihydrobenzo[b]furan-7-carboxylic acid chlorides or esters with appropriate amines and recovering the carboxamides as acid salts An alternative method of preparing the compounds utilizes an appropriately substituted benzofuran carboxylic acid which is reacted with ethyl chloroformate to form a mixed anhydride of the acid which is subsequently reacted with a solution of the amine (e.g., in dichloromethane). This method simplifies the synthesis where the carboxylic acid includes one or more substituents, such as an amino group, which is capable of reacting with the carboxyl group in competition with the amine. The synthesis of selected compounds is shown in the following examples.

EXAMPLE 1

Preparation of
N-(1-azabicyclo[2.2.2]oct-3-yl)4-Amino-5-Chloro
-2,3-Dihydrobenzo[b]Furan-7-Carboxamide,
Compound No. 77

A suspension of 4-amino-7-carboxy-5-chloro -2,3-dihydrobenzofuran (16.02g 75 mmol.) and 1,1-carbonyl-diimidazole (12.16 g. 75 mmol.) in 300 ml of tetrahydrofuran (THF) was stirred at room temperature under argon overnight. To this there was added 9.87 g (75.0 m mol.) of 3-aminoquinuclidine (available as the R or S isomer from Chiron Laboratory, Norway) available from Aldrich Chemical as the racemate) in 50 ml of THF. The mixture was stirred at room temperature for three hours and then refluxed overnight.

Thin layer chromatography showed the reaction was incomplete and another 0.5 g of 3-aminoquinuclidine was added. The mixture was refluxed for another hour. The solvent in the mixture was evaporated and the residue dissolved in 1N HCl(150 ml), washed with $CH_2Cl_2$ (2×100 ml). The aqueous layer was made alkaline with 2N NaOH and extracted with $CH_2Cl_2$ (3×200 ml). The organic layers were combined and were dried over anhydrous magnesium sulphate and evaporated to give 8.13 g of the free base.

To a methanol (50 ml) solution of the free base there was added 1.46 g of fumaric acid. The mixture was stirred for one (1) hour before ether (120 ml) was added and then left in the freezer overnight The resulting precipitate was collected by filtration and dried to give 8 28 g of a white solid M.W.=397.86, m.p.=216-217° C.

EXAMPLE 2

Preparation of N-(1-azabicyclo2 2.2]oct-3-yl)5-Chloro
-2,3-Dihydrobenzo[b]Furan-7-Carboxamide,
Compound No. 90

A mixture of 7-carboxy-5-chlorodihydrobenzofuran (5.96g , 30 mmol ) and 1,1-carbonyldiimidazole (4.86g 30 mmol.) in 120 ml of THF was stirred at room temperature for 2 hours, under argon. To this there was added a THF (30 ml) solution of 3-aminoquinucludine (3.75 g. 30 mmol ) The solution was heated to reflux overnight The solvent in the solution was evaporated and the residue was dissolved in 300 ml of $CH_2Cl_2$. The $CH_2Cl_2$ solution was washed with sodium bicarbonate (1×75 ml), brine (1×50 ml), dried over anhydrous magnesium sulphate and evaporated to give 7.39 g of a solid (80.3% yield) To this sample in 75 ml of methanol was added 1 molar equivalent of fumaric acid and the mixture was stirred at room temperature and left in the freezer overnight. The resulting precipitates were collected by filtration to give 8.2 g of a compound which was then recrystallized from 2-propanol/methanol. The product was collected on a filter to give 5 17 g as a white solid. The yield was 47.2% NMR spectral data suggested that this compound contained a half molar equivalent of fumaric acid, melting point 226-228° C.

As used herein, the phrase "active drug substance" (ADS) refers to the compounds described herein which are useful in the method of alleviating or preventing anxiety of the invention. The term "pharmaceutical dosage form" as used herein refers to the "finished" or formulated dosage form which comprises the active drug substance as well as pharmaceutically acceptable carriers, diluents, adjuvants and the like.

The active drug substance described herein may be administered orally or parenterally. Suitable pharmaceutically acceptable diluents, carriers, or adjuvants known in the art may be used to prepare anxiolytic compositions such diluents, carriers, etc. are generally a solid or liquid or a mixture of a solid and a liquid.

Solid form compositions or pharmaceutical dosage forms suitable for use herein include powders, granules, tablets, capsules (e.g. hard and soft gelatin capsules) filled with powders, granules, or in the case of a soft gelatin capsule, a liquid, suppositories and pessaries A solid carrier can be, for example, one or more substances which may also act as a lubricant, solubiliser, suspending agent, filler, glidant, compression aid, binder or tablet-disintegrating agent, it can also be an encapsulating material In powders, the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferable 1 to 80% of the active ingredient. Suitable solid carriers include, for example, calcium phosphate, magnesium stearate, talc, sugars, lactose, dextrin, starch, gelatin, cullulose, methyl cellulose, sodium carboxymethyl cellulose, polyvinylpyrrolidine, low melting waxes and ion exchange resins.

Liquid form compositions include, for example, solutions, suspensions, emulsions, syrups, elixirs and pressurized compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile parenteral solutions may be administered intravenously. When the active drug substance is administered intravenously (I.V.), most often the pharmaceutical dosage form will be a sterile lyophilizate which is reconstituted with a sterile pharmaceutical diluent prior to I.V. administration to the patient.

The compounds discussed herein have 5-$HT_3$ antagonism and are considered to be useful in treating anxiety as well as other psychotic disorders such as schizophrenia. These compounds may also be useful in the treatment of migraine and cluster headaches.

As used herein, the term "anxiolytically effective amount" refers to the concentration of the active drug substance in a pharmaceutically acceptable as well as biologically acceptable pharmaceutical dosage form effective to reduce or alleviate anxiety in a patient suffering from such condition. Such amount will vary from patient to patient depending on such factors as body weight, age, overall general health as well as a consideration of any other medications being administered to the patient at the same time.

In general, from about 0.001 mg about 60 mg per patient per day will be effective to control or alleviate anxiety would be recognized by the skilled physician or pharmacist, in elderly and debilitated patients, the dosage should be limited to the smallest effective amount. The term "anxiety" or "anxiety disorder" as used herein refers to a condition which is characterized by a feeling of apprehension and fear without apparent stimulus and is associated with physiological changes such as tackacardia, sweating, tremor, etc.

The following examples illustrate use of the compounds described herein in standard tests which have been found to be predictive of anxiolitic activity.

EXAMPLE 3

Methods

Male Hooded Lister rats (Bradford bred, 200-250 g) were housed 5 to a cage. Rats paired in the test were taken from separate cages.

Tests were conducted between 13.00 and 18.00 hr in an illuminated room using a methodology based on the model of File, *J. Neurosci. Meth.* 2: 219–238. The apparatus used for the detection of changes in rat social interaction and exploratory behaviour consisted of an open-topped box (51×51 cm and 20 cm high) with 17×17 cm areas marked on the floor. Two naive rats, from separate housing cages, were placed into the brightly illuminated area and their behaviour observed over a 10 min period by remote video recording. Two behaviours were noted, (1) social interaction between the animals was determined by timing (second), sniffing of partner, crawling under or climbing over partner, genital investigation of partner, following partner and (2) exploratory locomotion was measured as the number of crossings of the lines marked on the floor of the test box.

Under the conditions of unfamiliarity and high illumination, drugs were tested by treating both members of a pair of rats with the same treatment administered intraperitoneally as an acute single treatment at the predetermined time 40 min before testing.

Rats were tested with several of the compounds described herein initially at 1 ng/kg, 1 ug/kg and 1 mg/kg and subsequently at 0.1 and 0.01 ng/kg as considered appropriate. Diazepam (0.063-10 mg/kg single i.p. treatment), buspirone (0.25-1.0 mg/kg i.p. daily for 7 days) and ondansetron (0.0001-0.1 mg/kg single i.p. treatment) were used as positive controls.

Rats were used on a single occasion only in treatment groups of 6 pairs. Results were analyzed using single-factor analysis of variance with Dunnett's t-test for comparing multiple treatments with a single control and are presented as means E.M.S.

(RS)-Compound No. 75, (R)-Compound No. 75, (RS)-Compound No. 77, (R)-Compound No. 77, ondansetron and buspirone were dissolved in water and diluted with saline; diazepam was dissolved in the minimum quantity of HCl, neutralized and made up to volume with saline. All drugs were administered as the base in a volume of 1 ml/kg body weight.

Changes in behaviours indicative of an anxiolytic potential were indicated as increases in social interaction. A change in line crossings indicated a change in locomotor activity. The results are shown in the Table 2.

TABLE 2

The Ability of Compounds to Enhance Social Interaction in the Rat

| Drug | Dosage (mg/kg) | Social Interaction Time | Locomotion Activity (Crossing) |
|---|---|---|---|
| Diazepam | — | 75 | 120 |
|  | 0.63 | 75 | 118 |
|  | 0.125 | 137 | 120 |
|  | 0.25 | 165 | 118 |
|  | 1.0 | 155 | 120 |
| Buspirone | — | 78 | 118 |
|  | 0.25 | 130 | 120 |
|  | 0.5 | 150 | 120 |
|  | 1.0 | 145 | 118* |
| Ondanestrone | — | 75 | 120 |
|  | .0001 | 90 | 125 |
|  | .001 | 16— | 120 |
|  | .01 | 158 | 140 |
|  | .1 | 155 | 120 |
| Compound No. 77(R) | — | 90 | 120 |
|  | .01 ng | 80 | 118 |
|  | .1 ng | 135 | 116 |
|  | 1 ng | 170 | 118 |
|  | 1 ng | 185 | 120 |

TABLE 2-continued

The Ability of Compounds to Enhance Social Interaction in the Rat

| Drug | Dosage (mg/kg) | Social Interaction Time | Locomotion Activity (Crossing) |
|---|---|---|---|
| Compound No. 77 (RS) | — | 90 | 120 |
|  | .1 ng | 95 | 120 |
|  | 1 ng | 115 | 118 |
|  | 1 ug | 155 | 118 |
|  | 1 mg | 170 | 118 |
| Compound 75 (R) | — | 75 | 120 |
|  | .01 ng | 80 | 122 |
|  | .1 ng | 160 | 120 |
|  | 1 ng | 175 | 122 |
|  | 1 ug | 185 | 120 |
| Compound 75 (RS) | — | 75 | 118 |
|  | 0.1 ng | 85 | 120 |
|  | 1 ng | 110 | 120 |
|  | 1 ug | 175 | 120 |
|  | 1 mg | 180 | 120 |

*Dosage in mg/ml unless otherwise indicated
n = 6 pairs
P < 0.001

As can be seen from the data presented in Table 2, diazepam (marketed under the trademark "VALIUM" by Roche) administered as a single dose in the range of 0.125–1.0 mg/kg administered i.p. enhanced social interaction with no change in locomotor activity. The use of a higher dose of 10 mg/kg was associated with marked reductions in locomotor response. It has been found that buspirone fails to consistently increase social interaction in the rat when administered as an acute treatment. But on repeated daily administrations, as indicated by the 7 day treatment described in Example 3, increases in social interaction occurred within a dose range of 0.25 to 1.0 mg/kg i.p.; there were no changes in locomotor activity. Both diazepam and buspirone maximally increased social interaction to 150 sec, approximate to a 200% increase compared to vehicle treated control animals. A single administration of ondanestrone (1 ug/kg i.p.) caused an increase in social interaction of similar intensity but was 100 to 1,000 times more potent, with no changes in locomotor activity.

Compound No. 77(R) and (R,S) and Compound No. 75(R) and (R,S) increased social interaction in the rate in the complete absence of sedation or motor impairment. Minimally effective doses of (R)-Compound No. 77 and (R)-Compound No. 75 were 0.1 ng(nanogram)/kg i.p.; (RS)-compound 77 and (RS)-compound 75 were effective at 1.0ng(nanogram)/kg. The effects of all four compounds were found across an extended dose range to the maximum dose attempted of 1 mg/kg. The compounds therefore were fully effective over at least a million-fold dose range. The compounds were approximately one million times more potent than diazepam and buspirone, and 100 to 1,000 times more potent than ondansetron.

EXAMPLE 4

Black:White Test Box

Anxiety can be induced in mice by placing them in an aversive environment (bright illumination). This test has been used to define the anxiolytic profile of known clinically active anxiolytic agents (Costall et al., *Pharmacol Biochem Behav* 32:777–785, 1989) and the selectivity of the test procedure has been established using a wide range of psychoactive agents (Costall et al., *Pharmacol Biochem Behav* 32:777–785, 1989).

The following example illustrates this procedure in greater detail utilizing several of the compound described herein.

Adult male albino mice (BKW, Bradford bred) 35–40g were used in this example. Mice were group housed (n=10) on a 12 hour light/dark cycle for at least 7 days prior to testing. Food and water were allowed ad libitum. Behavioural testing was carried out between 11.00 and 16.00 hour in a darkened room illuminated with red light only. On the day of testing mice were taken from the darkened holding room in an enclosed trolley to the darkened testing room and allowed a 2 hour period of adaptation to the new environment.

The apparatus used for the assessment of behavioural change consisted of an open-topped box (45×27×27 cm high) two-fifths painted black and illuminated by dim red light (1×60W) and partitioned from the remainder of the box which was painted white and brightly illuminated with a 60W light source located 17 cm above the box. A 7.5 cm×7.5 cm opening was located at floor level in the centre of the partition, allowing access between the two compartments, each of which was lined into 9 cm squares.

At the Start of behavioural testing the mice were placed individually into the centre of the white, brightly lit area of the test box. The mice were observed over a 5 min. period by remote video recording. Four behaviours were recorded:

1. The number of exploratory rearings in the white and black sections.
2. The number of line crossings in the white and black areas.
3. The time spent in the black area.
4. The latency of the initial movement from the white (W) to the black (B) area.

The compounds or the saline vehicle were administered to the mice via the intraperitoneal route 40 min prior to testing. The benzodiazepine anxiolytic, diazepam (0.063–10 mg/kg i.p.), the anxiolytic buspirone (0.063–2 mg/kg i.p.) and ondansetron (0.01 ng/kg–10 ug/kg i.p.) and zacopride (0.0001 mg/kg–10 mg/kg i.p.) were used as positive controls.

Mice were used on one occasion only in treatment groups of 5. Results were analyzed using single-factor analysis of variance with Dunnett's t-test for comparing multiple treatments with a single control and are presented as mean+S.E.M.s (% time data-analyses on original data).

Drugs (RS) Compound No. 77, (R) Compound No. 77, (S) Compound No. 77, (R,S) Compound No. 75, (R) Compound No. 75, (S) Compound No. 75, buspirone, ondansetron and zacopride were dissolved in saline, diazepam was dissolved in the minimum quantity HCl, neutralized and made up to volume with saline. All drugs were administered as the base in a volume of 1 ml/100 g body weight.

Changes in behavioural responding indicative of an anxiolytic potential are indicated as an increase in exploratory behaviour (rears and line crossings) in the white section of the test box with a concomitant decrease in these parameters in the black section also a reduced latency to enter the dark section and a decrease in the % time spent in the black section. The results of this example are set forth in Tables 3–12. In the tables S1–S6 are the standard deviation for the data in the adjacent left hand column.

TABLE 3

Drug Response Black White Box Test
Compound 75

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 23.000 | 2.500 | 90.300 | 9.500 | 28.000 | 3.000 | 96.700 | 10.300 | 59.000 | 6.000 | 5.000 | 0.800 |
| 2. | 1 ng/kg i.p. | 34.600 | 3.700 | 78.000 | 8.000 | 38.800 | 4.200 | 79.000 | 8.000 | 56.000 | 5.700 | 9.500 | 1.200 |
| 3. | 100 ng/kg i.p. | 30.000 | 3.600 | 82.000 | 8.400 | 33.000 | 3.700 | 80.000 | 8.800 | 59.600 | 6.100 | 7.000 | 0.800 |
| 4. | 1 ug/kg i.p. | 79.000 | 8.200 | 26.000 | 2.800 | 80.700 | 8.300 | 30.600 | 3.100 | 30.600 | 3.100 | 18.000 | 2.000 |
| 5. | 100 ug i.p. | 87.000 | 9.000 | 28.000 | 3.000 | 89.000 | 9.200 | 29.000 | 3.000 | 26.000 | 2.800 | 20.000 | 2.200 |
| 6. | 1 mg/kg i.p. | 99.000 | 11.000 | 25.000 | 2.700 | 102.000 | 10.600 | 27.000 | 2.900 | 26.600 | 2.900 | 21.600 | 2.200 |

TABLE 4

Drug Response Black White Box Test
Compound 75 (R-isomer)

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 17.000 | 1.900 | 99.000 | 10.700 | 26.500 | 2.700 | 112.000 | 13.000 | 65.000 | 6.700 | 6.000 | 0.700 |
| 2. | 0.01 ng/kg i.p. | 20.000 | 2.100 | 96.000 | 10.200 | 26.000 | 2.700 | 112.000 | 13.000 | 62.000 | 6.400 | 7.000 | 0.800 |
| 3. | 0.1 ng/kg i.p. | 41.000 | 4.300 | 59.000 | 5.900 | 50.000 | 5.300 | 63.000 | 6.500 | 40.000 | 4.100 | 13.000 | 1.400 |
| 4. | 1 ng/kg i.p. | 60.000 | 6.300 | 30.000 | 3.300 | 70.000 | 7.300 | 44.000 | 4.800 | 33.000 | 3.600 | 12.600 | 1.400 |
| 5. | 1 ug/kg i.p. | 80.000 | 8.200 | 25.000 | 2.000 | 88.000 | 9.100 | 24.000 | 2.600 | 32.000 | 3.300 | 12.000 | 1.300 |
| 6. | 100 ug/g i.p. | 72.000 | 7.600 | 26.000 | 2.800 | 81.000 | 8.300 | 27.000 | 3.000 | 27.000 | 2.800 | 12.500 | 1.400 |
| | 1 mg/kg i.p. | 71.000 | 7.000 | 24.000 | 2.600 | 73.000 | 7.700 | 27.000 | 2.800 | 32.000 | 3.400 | 12.000 | 1.300 |

TABLE 5

Drug Response Black White Box Test
Compound 75 (S-isomer)

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 23.000 | 2.500 | 90.300 | 9.500 | 28.000 | 3.000 | 96.700 | 10.300 | 59.000 | 6.000 | 5.000 | 0.600 |
| 2. | 1 ng/kg i.p. | 27.000 | 3.000 | 87.000 | 9.000 | 34.700 | 3.600 | 99.000 | 11.700 | 56.000 | 5.700 | 9.000 | 1.100 |
| 3. | 1 ug/kg i.p. | 25.300 | 2.800 | 92.000 | 9.700 | 29.600 | 3.400 | 98.000 | 10.300 | 56.000 | 5.700 | 4.800 | 0.600 |
| 4. | 1 mg/kg i.p. | 98.000 | 10.700 | 24.600 | 2.700 | 104.000 | 11.300 | 25.200 | 2.700 | 22.000 | 2.400 | 19.600 | 2.000 |
| 5 | Diaz 0.25 mg | 89.000 | 9.300 | 26.000 | 2.800 | 92.000 | 10.300 | 28.600 | 3.000 | 26.000 | 2.800 | 20.100 | 2.300 |

TABLE 6

Drug Response Black White Box Test
Compound 77

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 22.000 | 2.400 | 95.000 | 10.200 | 28.000 | 2.900 | 102.000 | 11.000 | 56.500 | 5.800 | 5.200 | 0.600 |
| 2. | 1 ng/kg i.p. | 30.000 | 3.200 | 87.000 | 8.800 | 36.000 | 3.900 | 93.000 | 9.700 | 50.000 | 5.200 | 6.000 | 0.700 |
| 3. | 100 ng/kg i.p. | 73.000 | 7.600 | 29.000 | 3.100 | 94.000 | 9.800 | 33.000 | 3.600 | 33.000 | 3.600 | 18.000 | 2.100 |
| 4. | 1 ug/kg i.p. | 96.000 | 10.300 | 22.000 | 2.300 | 117.000 | 12.200 | 23.300 | 2.500 | 24.000 | 2.600 | 26.600 | 2.900 |
| 5. | 100 ug/kg i.p. | 90.000 | 9.300 | 19.000 | 2.200 | 110.000 | 13.000 | 21.000 | 2.300 | 23.000 | 2.600 | 25.000 | 2.600 |
| 6. | 1 mg/kg i.p. | 102.000 | 11.000 | 17.000 | 1.900 | 127.000 | 13.200 | 22.000 | 2.300 | 25.000 | 2.700 | 28.600 | 3.000 |

TABLE 7

Drug Response Black White Box Test
Compound 77 (R-isomer)

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 19.300 | 2.000 | 93.000 | 9.600 | 24.000 | 2.600 | 102.000 | 11.000 | 60.000 | 6.300 | 8.000 | 0.900 |
| 2. | 0.01 ng/kg i.p. | 22.000 | 2.200 | 90.000 | 9.300 | 31.000 | 3.300 | 103.000 | 11.000 | 60.000 | 6.500 | 9.000 | 1.100 |
| 3. | 0.1 ng/kg i.p. | 73.000 | 7.500 | 28.000 | 3.000 | 90.000 | 10.000 | 30.000 | 3.100 | 26.200 | 2.700 | 17.000 | 2.000 |
| 4. | 1 ng/kg i.p. | 83.000 | 8.400 | 28.000 | 3.100 | 97.000 | 10.300 | 24.000 | 2.600 | 27.000 | 2.800 | 17.000 | 2.000 |
| 5. | 1 ug/kg i.p. | 87.000 | 9.000 | 21.000 | 2.300 | 109.000 | 11.700 | 23.000 | 1.900 | 30.000 | 3.200 | 19.000 | 2.000 |
| 6. | 100 ug/kg i.p. | 83.000 | 8.600 | 21.000 | 2.300 | 106.000 | 11.000 | 26.000 | 2.800 | 25.000 | 2.600 | 23.000 | 2.600 |
| 7. | 1 mg/kg i.p. | 80.000 | 8.300 | 22.000 | 2.400 | 94.000 | 10.300 | 34.000 | 3.600 | 27.000 | 2.900 | 23.000 | 2.600 |

TABLE 8

Drug Response Black White Box Test
Compound 77 (R-isomer)

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 19.300 | 2.000 | 93.000 | 9.600 | 24.000 | 2.600 | 102.000 | 11.000 | 60.000 | 6.300 | 8.000 | 0.900 |
| 2. | 1 ng/kg i.p. | 22.000 | 2.400 | 88.000 | 9.100 | 25.000 | 2.600 | 100.000 | 10.500 | 64.000 | 6.600 | 7.800 | 0.900 |
| 3. | 1 ug/kg i.p. | 20.000 | 2.300 | 91.000 | 9.600 | 24.000 | 2.500 | 101.000 | 11.000 | 61.000 | 6.300 | 7.200 | 0.900 |
| 4. | 1 mg/kg i.p. | 17.700 | 1.800 | 88.000 | 9.000 | 27.000 | 2.900 | 98.000 | 9.900 | 60.000 | 6.200 | 10.000 | 1.300 |
| 5. | Diaz 0.25 mg | 80.000 | 8.400 | 24.000 | 2.600 | 86.000 | 9.700 | 30.000 | 3.100 | 26.000 | 2.700 | 19.000 | 2.000 |

TABLE 9

Drug Response Black White Box Test
Diazepan

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 23 | 2.6 | 70 | 7.3 | 39 | 3.6 | 78 | 8.3 | 56 | 5.4 | 10 | 1.0 |
| 2. | 0.63 | 29 | 2.9 | 72 | 7.1 | 40 | 3.7 | 74 | 7.4 | 57 | 5.3 | 10 | 1.1 |
| 3. | .125 | 64 | 6.6 | 23 | 2.4 | 77 | 7.9 | 29 | 2.6 | 28 | 3.0 | 20 | 2.1 |
| 4. | .25 | 70 | 7.6 | 19 | 1.5 | 80 | 9.1 | 22 | 1.9 | 27 | 3.0 | 27 | 3.2 |
| 5. | .5 | 72 | 8.2 | 17 | 1.8 | 83 | 8.7 | 20 | 1.7 | 24 | 3.1 | 26 | 2.8 |
| 6. | 1 | 73 | 8.1 | 17 | 1.5 | 80 | 9.3 | 21 | 1.8 | 25 | 3.0 | 25 | 2.9 |
| 7. | 10 | 18 | 1.9 | 13 | 1.3 | 20 | 2.6 | 20 | 1.3 | 22 | 3.0 | 27 | 3.6 |

TABLE 10

Drug Response Black White Box Test
Buspirone

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | V | 22.400 | 1.500 | 89.000 | 2.760 | 21.800 | 1.070 | 98.600 | 1.750 | 64.900 | 1.900 | 5.600 | 0.510 |
| 2. | .125 | 24.600 | 2.290 | 83.800 | 2.690 | 27.000 | 1.730 | 124.000 | 7.090 | 63.600 | 0.800 | 5.600 | 0.680 |
| 3. | .25 | 71.800 | 2.730 | 31.200 | 1.830 | 82.400 | 4.130 | 30.800 | 1.390 | 37.700 | 1.300 | 17.200 | 1.960 |
| 4. | .5 | 82.000 | 1.230 | 25.800 | 1.930 | 102.800 | 4.330 | 25.200 | 1.320 | 32.900 | 2.400 | 21.000 | 1.610 |
| 5. | 1 | 83.200 | 1.720 | 28.600 | 1.970 | 89.200 | 3.120 | 23.000 | 2.760 | 32.600 | 1.600 | 21.200 | 1.930 |
| 6. | 2 | 21.200 | 2.460 | 10.600 | 2.840 | 16.000 | 1.300 | 10.600 | 2.250 | 26.500 | 5.200 | 27.800 | 4.440 |

TABLE 11

Drug Response Black White Box Test
Odansetron

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | C | 24 | 2.5 | 70 | 7.1 | 36 | 3.7 | 79 | 7.6 | 55 | 5.5 | 11 | 1.2 |
| 2. | .01 | 29 | 2.9 | 69 | 6.9 | 38 | 3.9 | 81 | 8.3 | 54 | 5.5 | 10 | 1.0 |
| 3. | .05 | 74 | 7.6 | 20 | 2.0 | 76 | 7.9 | 20 | 2.0 | 26 | 2.6 | 26 | 2.6 |
| 4. | .1 | 81 | 8.3 | 17 | 1.7 | 94 | 9.3 | 16 | 1.6 | 20 | 2.0 | 30 | 3.6 |
| 5. | 1 | 82 | 8.4 | 16 | 1.5 | 80 | 8.3 | 17 | 1.9 | 21 | 2.3 | 29 | 2.9 |
| 6. | 10 | 81 | 8.1 | 19 | 1.9 | 90 | 9.1 | 18 | 2.0 | 20 | 2.0 | 29 | 3.0 |

TABLE 12

Drug Response Black White Box Test
Zacopride

| | Drug/Dose | Rearings White | S1 | Rearings Black | S2 | Crossings White | S3 | Crossings Black | S4 | % Time Black | S5 | Latency Time White | S6 |
|---|---|---|---|---|---|---|---|---|---|---|---|---|---|
| 1. | V | 26.600 | 2.560 | 83.000 | 3.520 | 27.800 | 1.720 | 102.800 | 4.380 | 62.600 | 3.100 | 6.600 | 0.810 |
| 2. | .0001 | 51.400 | 3.080 | 38.000 | 2.300 | 48.600 | 3.190 | 49.600 | 2.980 | 38.300 | 1.500 | 13.400 | 2.020 |
| 3. | .001 | 83.600 | 2.560 | 30.400 | 2.580 | 104.200 | 6.820 | 30.800 | 3.020 | 31.000 | 2.300 | 21.800 | 1.460 |
| 4. | .05 | 84.000 | 3.910 | 28.000 | 2.950 | 87.000 | 4.060 | 30.000 | 1.920 | 33.900 | 1.400 | 21.200 | 2.350 |
| 5. | .1 | 83.400 | 2.640 | 31.800 | 2.630 | 94.400 | 6.380 | 30.400 | 1.290 | 30.300 | 2.500 | 20.400 | 0.750 |
| 6. | 1 | 85.600 | 2.400 | 27.400 | 2.230 | 93.000 | 6.140 | 29.800 | 3.020 | 29.400 | 2.300 | 25.400 | 2.140 |
| | 10 | 84.600 | 2.250 | 29.600 | 2.790 | 91.000 | 2.670 | 24.200 | 0.490 | 31.600 | 2.000 | 23.000 | 1.480 |

The data set forth above illustrates that Compound No. 77 and Compound No. 75 induce behavioural changes in the black:white test box which would indicate that they possess anxiolytic potential. The R-isomers of Compound No. 77 and Compound No. 75 potently induced changes in behavioural responding which are indicative of anxiolytic activity while the S-isomers remained essentially inactive.

One major difference between the profile of action of the Compounds described herein and the known anxiolytics diazepam and buspirone is the lack of development of sedation. Additionally, there was no indication of a loss of efficacy at higher doses (bell-shaped curve).

While the present invention has been described in detail and by reference to specific embodiments thereof, it will be recognized that numerous modifications and variations are possible without departing from the scope of the invention as defined by the following claims.

What is claimed is:

1. A method for the treatment of anxiety comprising orally or parenterally administering to a patient in need of such treatment an anxiolytically effective amount of a compound of the formula (I) or a pharmaceutically acceptable salt thereof

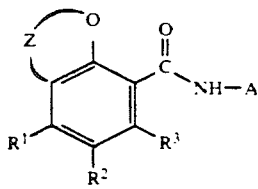

wherein Z represents the carbon and hydrogen atoms necessary to complete a substituted or unsubstituted, saturated or unsaturated, 5-membered ring; $R^1$, $R^2$, and $R^3$ may be the same or different and represent a member selected from the group consisting of hydrogen, lower alkyl, cycloalkyl, lower alkoxy, amino, lower alkyl substituted amino, acylamido, sulfonamido, halogen, and nitro; A represents moiety selected from the group consisting of formulas (II) and (VII).

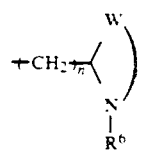

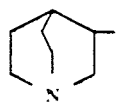

wherein W represents a single bond or the carbon and hydrogen atoms necessary to complete a 3- to 8-membered saturated or unsaturated ring; $R^6$ is selected from the group consisting of hydrogen, lower alkyl, phenyl, phenalkyl, fluorine-substituted alkyl, propargyl, and allyl; and n is 0 or an integer of 1 to 3; provided that when Z represents the atoms necessary to complete a 2,2-dimethyl-2,3-dihydrobenzofuran ring, $R^1$, $R^2$ and $R^3$ may not simultaneously equal hydrogen and when $R^2$ is flourine, $R^1$ and $R^3$ may not equal hydrogen.

2. The method of claim 1 wherein A is represented by the formula II.

3. The method of claim 2 wherein A is represented by the formula (IIa)

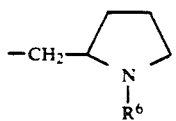

Where $R^6$ is defined as in claim 1.

4. The method of claim 3 wherein Z represents the atoms necessary to complete an unsubstituted dihydrofuran ring.

5. The method of claim 4 wherein one of $R^1$ and $R^2$ is amino.

6. The method of claim 5 wherein $R^6$ is hydrogen.

7. The method of claim 5 wherein $R^6$ is ethyl.

8. The method of claim 6 wherein $R^1$ is amino, $R^2$ is chloro and $R^3$ is hydrogen.

9. The method of claim 7 wherein $R^1$ is amino, $R^2$ is chloro and $R^3$ is hydrogen.

10. The method of claim 1 wherein A is represented by the formula (VII).

11. The method of claim 9 wherein Z represents the atoms necessary to complete an unsubstituted dihydrofuran ring.

12. The method of claim 10 wherein one of $R^1$, $R^2$ and $R^3$ is an amino group.

13. The method of claim 11 wherein $R^1$ is amino, $R^2$ is chloro and $R^3$ is hydrogen.

14. The method of claim 11 wherein $R^1$ and $R^3$ are hydrogen and $R^2$ is chloro.

15. The method of claim 11 wherein $R^1$ and $R^2$ are hydrogen and $R^3$ is methoxy.

16. The method of claim 1 wherein said compound is represented by the formula VIII.

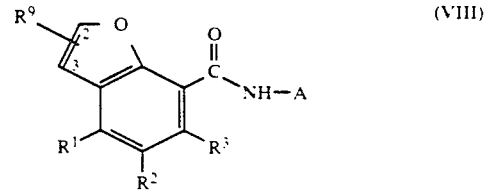

where A, $R^1$, $R^2$ and $R^3$ are defined as in claim 1 and $R^9$ is hydrogen, lower alkyl, cycloalkyl or phenyl.

17. The method of claim 1 wherein said compound is represented by the formula (IX)

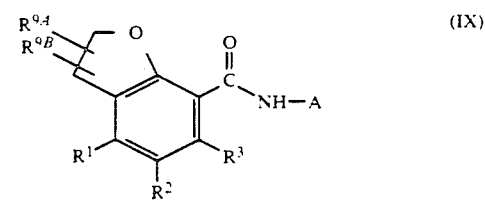

where A, $R^1$, $R^2$ and $R^3$ are defined as in claim 1 and $R^{9A}$ and $R^{9B}$ are independently hydrogen, lower alkyl, cycloalkyl or phenyl.

18. The method of claim 17 wherein A is represented by the formula (IIa)

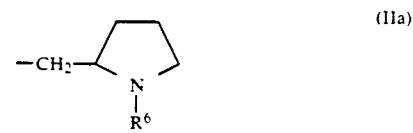

where $R^6$ is defined as in claim 1.

19. The method of claim 18 wherein $R^6$ is hydrogen.

20. The method of claim 17 wherein A is represented by the formula (VII).

21. The method of claim 18 wherein one of $R^1$, $R^2$ and $R^3$ is amino.

22. The method of claim 20 wherein one of $R^1$, $R^2$ and $R^3$ is amino.

23. The method of claim 21 wherein $R^1$ is amino, $R^2$ is chloro and $R^3$ is hydrogen.

24. The method of claim 22 wherein $R^1$ is amino, $R^2$ is chloro and $R^3$ is hydrogen.

25. The method of claim 8 wherein said compound has the R configuration.

26. The method of claim 9 wherein said compound has the R configuration.

27. The method of claim 13 wherein said compound has the R configuration.

* * * * *